United States Patent
Goldish et al.

(10) Patent No.: US 9,301,688 B2
(45) Date of Patent: Apr. 5, 2016

(54) SYSTEM FOR SCREENING THE SKIN CONDITION OF THE PLANTAR SURFACE OF THE FEET

(71) Applicant: The United States Government, as Represented by the Department of Veterans Affairs, Washington, DC (US)

(72) Inventors: Gary D. Goldish, Plymouth, MN (US); Andrew Hansen, Apple Valley, MN (US); Eric Nickel, Chicago, IL (US)

(73) Assignees: The United States of America, as Represented by Dept. of Veterans Affairs, Washington, DC (US); Regents of University of Minnesota, Saint Paul, MN (US)

( * ) Notice: Subject to any disclaimer, the term of this patent is extended or adjusted under 35 U.S.C. 154(b) by 789 days.

(21) Appl. No.: 13/644,045

(22) Filed: Oct. 3, 2012

(65) Prior Publication Data

US 2013/0109951 A1    May 2, 2013

Related U.S. Application Data

(60) Provisional application No. 61/551,589, filed on Oct. 26, 2011.

(51) Int. Cl.
  *G03B 29/00* (2006.01)
  *G03B 41/00* (2006.01)
  *A61B 5/00* (2006.01)
(52) U.S. Cl.
  CPC ............. *A61B 5/0077* (2013.01); *A61B 5/0082* (2013.01); *A61B 5/447* (2013.01); *A61B 5/6829* (2013.01); *A61B 5/70* (2013.01)
(58) Field of Classification Search
  USPC ............................................ 396/14; 600/592
  See application file for complete search history.

(56) References Cited

U.S. PATENT DOCUMENTS 5,168,634 A * 12/1992 Misevich .......................... 33/515
5,790,256 A *  8/1998 Brown et al. .................. 356/613
(Continued)

FOREIGN PATENT DOCUMENTS

EP    1490651 B1    12/2004
FR    2730403 A1    8/1996
(Continued)

OTHER PUBLICATIONS

Hazenberg, C.E.V.B. et al, "The Validity and Reliability of Diagnosing Foot Ulcers and Pre-Ulcerative Lesions in Diabetes Using Advanced Digital Photography", Diabetes Technology & Therapeutics, vol. 12, No. 12, Department of Surgery Ziekenhuisgroep Twente, Almelo, The Netherlands (2010).
(Continued)

*Primary Examiner* — Clayton E Laballe
*Assistant Examiner* — Warren K Fenwick
(74) *Attorney, Agent, or Firm* — Gorman Law Offices; Robert Gorman

(57) ABSTRACT

The present invention relates to a novel approach means of screening foot skin condition of patients at risk for foot tissue breakdown, such as persons with diabetes, through the provision of a remote screening device that can be used in telemedicine or home self-monitoring approaches. The invention would record high resolution images of the bottom of the patient's feet, without artifacts or other distortions that might arise from images taken of feet that have been compressed through standing and the like. These images could immediately be viewed by the patient and/or electronically submitted to a medical facility where clinicians could screen the images for signs of tissue breakdown.

10 Claims, 4 Drawing Sheets

(56) References Cited

U.S. PATENT DOCUMENTS

| | | | | |
|---|---|---|---|---|
| 5,941,835 | A * | 8/1999 | Sundman | 600/592 |
| 5,944,676 | A * | 8/1999 | Grassi | 602/23 |
| 7,068,379 | B2 | 6/2006 | Sundman et al. | |
| 7,976,482 | B2 * | 7/2011 | Mayr | 600/595 |
| 2004/0168329 | A1 | 9/2004 | Ishimaru | |
| 2005/0097762 | A1 | 5/2005 | Biesbrouck et al. | |
| 2006/0201011 | A1 * | 9/2006 | Katsu et al. | 33/512 |
| 2006/0245091 | A1 | 11/2006 | DeFazio | |
| 2008/0114269 | A1 * | 5/2008 | Martindale et al. | 600/592 |
| 2010/0179450 | A1 * | 7/2010 | Abdullah | 600/587 |
| 2012/0053490 | A1 * | 3/2012 | Smith | 600/592 |

FOREIGN PATENT DOCUMENTS

| | | |
|---|---|---|
| WO | 2004002309 A1 | 1/2004 |
| WO | WO 2004/002309 A1 | 1/2004 |
| WO | WO 2010/128519 A1 | 11/2010 |
| WO | WO2012/030373 A1 | 3/2012 |

OTHER PUBLICATIONS

Hazenberg, C.E.V.B et al, "Assessment of foot disease in the home environment of diabetic patients using a new photographic foot imaging device", Journal of Medical Engineering & Technology, vol. 34, No. 1, pp. 43-50, Department of Surgery Ziekenhuisgroep Twente, Almelo, (Jan. 2010).

* cited by examiner

SYSTEM FOR SCREENING THE SKIN CONDITION OF THE PLANTAR SURFACE OF THE FEET

FIELD OF THE INVENTION

The present invention relates to a novel approach to improving the use of foot screening for diabetics by offering a system for screening the skin condition of the plantar surface of the feet.

BACKGROUND OF THE INVENTION

Diabetics and other related types of diseased patients often suffer from sores, ulcers, and other symptoms of diseases that affect extremities such as the foot. Such patients often have loss of foot sensation, limited mobility, and decreased vision, all of which impairs their ability to monitor the condition of the skin on the plantar surfaces of their feet using current technologies. As such, preventing ulcers, sores and the like, or catching the presence of the same early can improve treatment outcomes and reduce the need for extreme interventions, such as amputations, thereby both resulting in improved quality of life of patients and reduced medical costs.

Heretofore, approaches for evaluating the bottom of the feet for persons at risk of tissue breakdown have been limited in various ways. One known approach relates to the provision of a small mirror (approximate 3 inches in diameter) on the end of a long handle which would be used by the patient to inspect the bottom of their foot for indications of skin breakdown, whereupon they would call their podiatrist and schedule an appointment for a physical examination. However, this system does not offer a medical provider with images, such that any assessment is made without the aid of a professional review, something which is especially problematic for someone with limited vision (e.g., especially from, say, diabetic retinopathy) given that such persons cannot readily discern the smaller, earlier signs of tissue breakdown. A similar system might involve use of a digital camera on the end of a flexible handle to aid in visualizing one's own skin for signs of pressure sores, and could possibly be made to send images to clinicians for telemedical evaluation or screening. Such a system, however, has several drawbacks, including the need for the camera and feet to remain stable during imaging.

A more advanced system has been developed in the Netherlands whereby users can image the soles of their feet, use a digital camera to image the soles of both feet, and automatically transmit the images to clinicians for evaluation. The system is contained within a box that reduces background light and uses LEDs to illuminate the feet for consistent lighting. This system, in addition to being expensive (and therefore being unlikely to receive extensive distribution as a home screening tool) utilizes horizontal bars for situation of the feet during picture acquisition, and these bars partially obstruct the full view of the feet. Furthermore, this system does not appear to show the image to the patient.

Other types of foot screening for diabetics are known in the art and often take the form of simple systems wherein a user can have pictures or the like taken of his feet while in a standing position. One such approach involves a system that allows patients to stand on a glass platform that scans an image of the plantar surface of the feet and provides this image of the same. The major drawback of this system is that the plantar tissues are pressed against the glass, thereby producing artifacts that can be misinterpreted as callous tissue, or which obscures the visualization of the earliest signs of skin breakdown (e.g. redness).

It is therefore, unknown in the art to provide a system for foot screening for diabetics where the user does not stand, or otherwise have his feet compressed against a support structure or platen. It is therefore a further problem in the art to provide screening method that does not compromise the image of the foot by compression on the plantar surface of the foot, thereby leading to artifacts or other distortions that will be present on the image of the plantar surface as a result of such compression. It is a further problem to provide a system that offers portable home screening that can interface electronically for telemedicine approaches. It is yet another problem in the prior art to provide a system that offers real time feedback to a user of the image being taken, so that he can review the results personally and also ensure that a treating physician can receive optimized images remotely, prior to transmission thereof.

SUMMARY OF THE INVENTION

From the foregoing, it is seen that it is a problem in the art to provide a device meeting the above requirements. According to the present invention, a device is provided which meets the aforementioned requirements and needs in the prior art by providing unobstructed and artifact-free images of the feet, for both the patient and his clinician to view.

The proposed invention therefore relates to a novel approach to improving the treatment of diabetics and other patients who may suffer from sores, ulcers, and other symptoms of diseases that affect extremities such as the foot. To this end, the present invention provides for the following beneficial advances relating to: (1) Provision of a screening method that does not compromise the image of the foot by compression on the plantar surface of the foot, thereby avoiding artifacts or other distortions that will be present on the image of the plantar surface as a result of such compression; (2) Provision of a screening method that offers portable home screening that can interface electronically for telemedicine approaches; (3) Provision of a screening method that offers real time feedback to a user of the image being taken, so that he can review the results personally and also ensure that a treating physician can receive optimized images remotely, prior to transmission thereof. To this end, the present invention overcomes the aforementioned and other disadvantages inherent in the prior art. Other objects and advantages of the present invention will be more readily apparent from the following detailed description when read in conjunction with the accompanying drawings.

DETAILED DESCRIPTION OF THE INVENTION

Figure 1A:
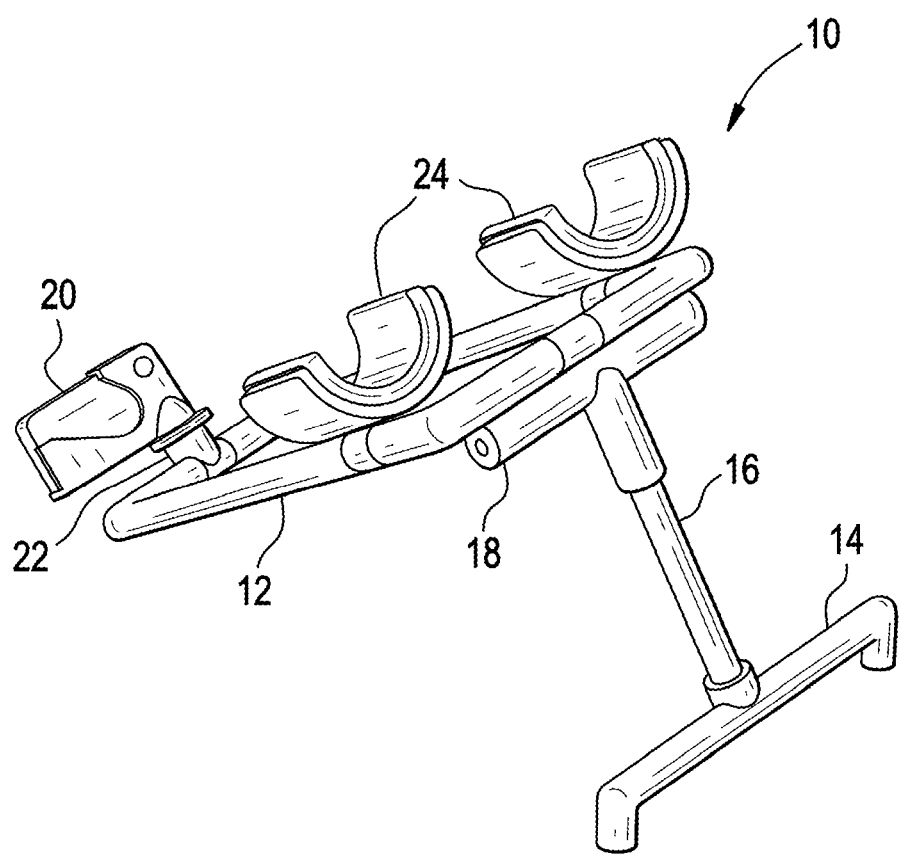
FIG. 1A is an offset elevated view of the system for screening the skin condition of the plantar surface of the feet according to the present invention.

The inventive purpose of the invention is to provide a means of screening foot skin condition of patients at risk for foot tissue breakdown (e.g. persons with diabetes) through the provision of a remote screening device that can be used in telemedicine or home self-monitoring approaches that can offer a solution that assists in the preventive monitoring and screening of patient feet. In addition, the apparatus is designed to be of a low enough cost so as to facilitate, in an economic fashion, the provision of such devices to all patients at risk for foot skin breakdown. The invention would be operated in the home where it would record high resolution images of the bottom of the patient's feet. These images could immediately be viewed by the patient and/or electronically submitted to a medical facility where clinicians could screen the images for signs of tissue breakdown. Frequent preventive checks using this device could therefore improve the rate of early detection of tissue breakdown and could potentially improve treatment outcomes and reduce the overall occurrence of severe interventions such as amputations and the like.

At its broadest level, the present invention is directed to a system for screening the skin condition of the plantar surface of the feet comprising: a support frame having a front portion, a rear portion, a left portion, a right portion, a top portion, and a bottom portion; a lower extremity support structure affixed to the support frame, so as to extend upwardly from the top portion of the support frame; and an image acquisition device interface affixed to the support frame, proximate to the rear portion of said support frame, the image acquisition device interface comprising retention framework for reception of, and stable retention of, an image acquisition device. In certain specific embodiments, the system for screening the skin condition of the plantar surface of the feet according the support frame may further include: (i) an elevation support framework for securely elevating said support frame substantially off a ground surface, either a static elevation stand or a foldable elevation stand hingably attached to the support frame at said front portion of said support frame; (ii) a lower extremity support structure that comprises two substantially parallel stabilizing leg cuffs; (iii) the retention framework for reception of, and stable retention of, an image acquisition device provides for the accommodation of said image acquisition device wherein the image acquisition device can be chosen from the group comprising cameras, camera-enabled smart phones, camera-enabled PDAs, and camera-enabled tablets; (iv) the support frame being at least partially formed from at least one lightweight material that is chosen from the group comprising aluminum, titanium, fiberglass, or plastic; (v) a directed illumination source and a remote trigger for triggering the image acquisition device and/or (vi) a monitor interface electronically connected to the image acquisition device for real time viewing of images acquired by said image acquisition device by an immediate user, whereby the monitor interface can, in one possible embodiment, be independently situated or alternatively, is affixed to the support frame so as to extend therefrom in an outwardly projected fashion for real time viewing of images acquired by said image acquisition device by an immediate user.

To this end, the inventive system for screening the skin condition of the plantar surface of the feet has additional features which further make it advantageous for patients when compared with conventional screening systems, in that it is portable and easily used at a home based setting, interfaces with many popular electronic devices such as laptops, iPads®, tablet PCs, PDAs, smart phones, cell phones and the like. Provision of such offers the advantage of not requiring physical situation in a clinical setting, and can limit personal visits by a patient for the purpose of ongoing screenings. To this end, the present invention overcomes the aforementioned and other disadvantages inherent in the prior art.

One embodiment would be a component in a formalized telemedicine system, prescribed by the podiatrist or other doctor for persons particularly at risk for skin problems on the feet. This type of system would involve a central platform with peripheral devices to monitor specific patient needs, and this inventive embodiment would therefore be a peripheral device for one or more of such telemedicine platforms. A different embodiment would entail instantiation as a stand-alone self-screening tool, and would accordingly be a less expensive version that could be designed using a simple digital camera with LEDs for directed illumination and a remote trigger with a basic display, such as the kind used by digital picture frames. The user could turn the system on, and then take a picture and it would immediately display on the provided hardware. One variant of this and other embodiments could also allow for simultaneous video-conferencing with the clinician using the built-in camera capabilities of say, an iPad® or other electronic device. Other variants could cover the spectrum in between the two aforementioned embodiments. For example, the present inventive system might contemplate the inclusion of a dedicated hardware platform capable of independent transmission via the internet through either a wireless phone data plan, or through wireless internet would provide the telemedicine capability without requiring the use of a particular telemedicine platform.

Another embodiment might contemplate provision of a means of interfacing with an advanced mobile phone, so as to use the unit as both the imaging device and the means of transmission. An alternative approach to visualizing the feet would be to send the image to the user's own computer, enabling him to use a larger monitor to display a larger image. The use of real-time streaming images would allow the user to shift their feet to better visualize any questionable irregularities. In yet another alternative embodiment, provision of multiple image acquisition devices (e.g., cameras, video cameras, webcams) could permit the use of lower resolution cameras, with each focused on one foot from a closer distance, effectively obtaining higher overall resolution, without significantly increasing cost. The user could then switch between images of each foot, or could stitch the images together into a single composite image so as to permit visualization of both feet on one screen. The use of a tablet hardware platform (such as the aforementioned iPad®) would permit easy zooming, which would be particularly useful for persons with reduced vision. As an alternative, large simple buttons on a touch screen of the electronically connected monitor could act in a similar manner.

Figure 1B:
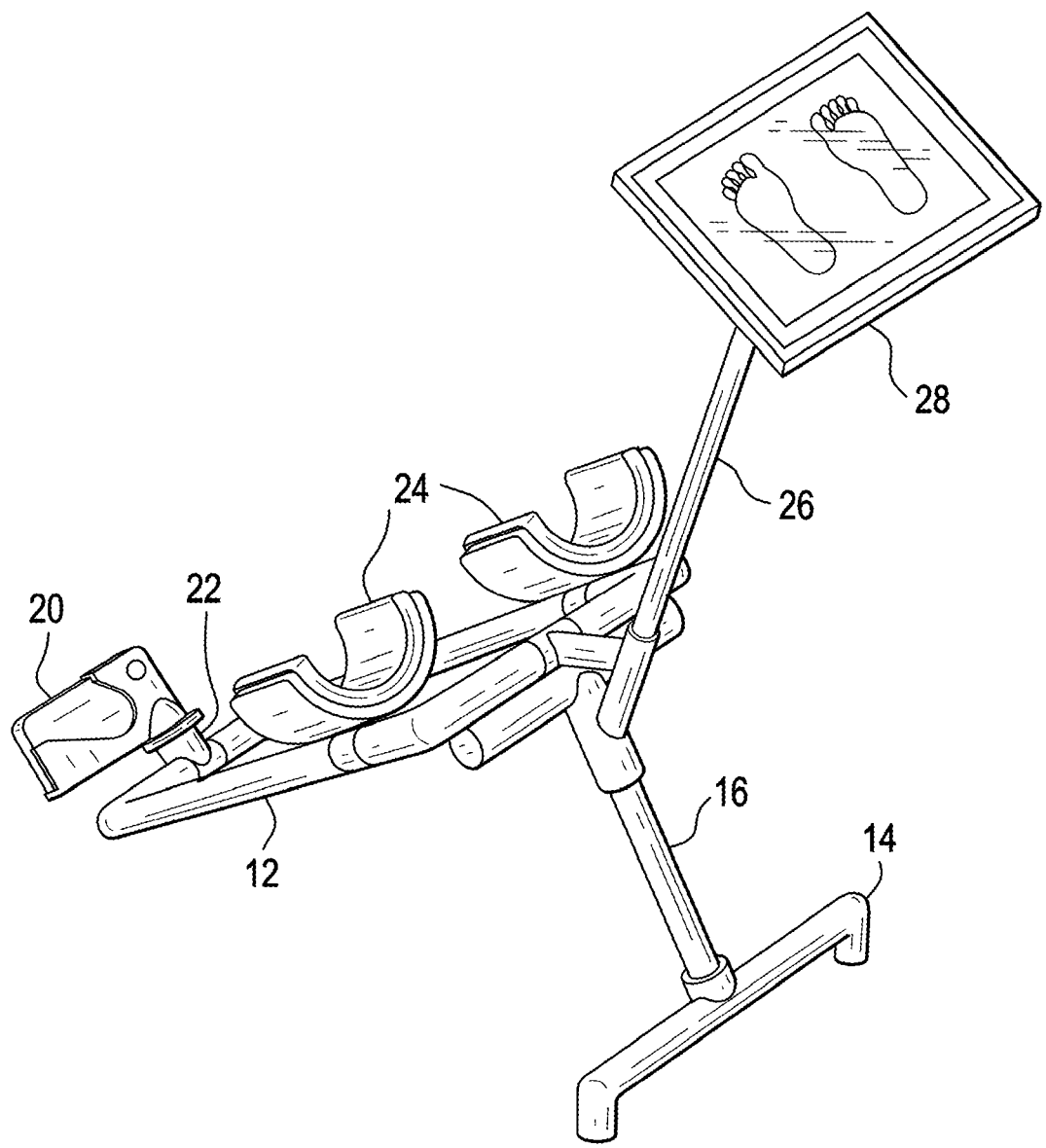
FIG. 1B is an offset elevated view of the system for screening the skin condition of the plantar surface of the feet according to the present invention with an optional monitor interface built thereon.
Figure 2:
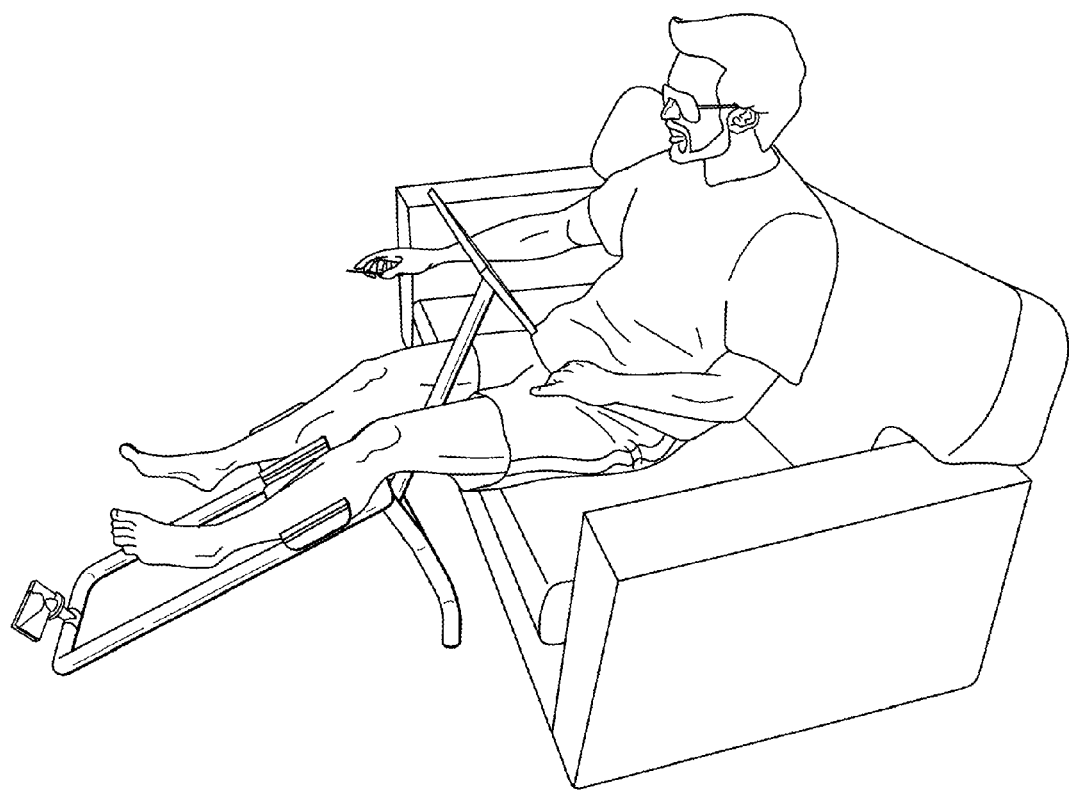
FIG. 2 is an offset elevated view of the system for screening the skin condition of the plantar surface of the feet according to the present invention with an optional monitor interface built thereon, and a user illustratively employing the same in a seated position from a chair during said usage.
Figure 3:
FIG. 3 is an offset elevated view of the system for screening the skin condition of the plantar surface of the feet according to the present invention with the aid of an electronic viewing device, such as a computer with a monitor or the like connected thereto, thereby eliminating the need for the aforementioned built in optional monitor interface of FIGS. 1B and 2, and a user illustratively employing the same in a seated position from a chair during said usage.

Thus, as seen in FIGS. 1A and 1B, and in figures described hereafter, each of the components of the present invention are more specifically discussed in greater detail below. In providing the above, the inventive system for screening the skin condition of the plantar surface of the feet 10 is therefore structured through the use of support frame 12 with lower extremity support structure 24 that supports the legs and feet of the user. Support frame 12 may have an elevation support framework 14, 16 for securely elevating said support frame substantially off a ground surface. Note that elevation support framework 14, 16 may be either a static elevation stand (not depicted, but may comprise fixed legs or walls) or as depicted, can be a foldable elevation stand hingably attached 18 to support frame 12 at the front portion of support frame 12. In either case, it can, like support frame 12, be at least partially formed from at least one lightweight material that is chosen from the group comprising aluminum, titanium, fiberglass, or high strength plastic. Lower extremity support structure 24 may be affixed on support frame 12 so as to extend in a generally upward fashion so as to support a user's lower extremities in an elevated fashion over support frame 12. As depicted, lower extremity support structure 24 may comprise two substantially parallel stabilizing leg cuffs, but as can be appreciate, alternative structures may also be employed with similar results, as long as the correct amount of overall stabilization is provided so that any images taken of the feet are not blurred from user movement, but in one embodiment, parallel stabilizing leg cuffs support the legs of the user closer to the ankles, because support of the legs closer to the ankle area (rather than on say, the calf area) situates image acquisition device 20 at a farther distance from the bottom of the user's feet which is some embodiments, can offer a more appropriate, stable position for the photographs or videos to be taken. Lower extremity support structure 24 is critical inasmuch as they support not only the lower legs, but also fully support or elevate the feet of a seated user on support frame 12 (use in the seated position is more generally depicted in FIGS. 2 and 3). Such a feature is important because it avoids the common weak points of known systems that acquire images from feet that have their plantar surfaces compressed on platens or other support structures, thereby leading to artifacts and other distortions in images. Opposite Lower extremity supports 24 is image acquisition device 20, which is normally a digital imaging device such as the camera or camera-enabled devices as described above, that are used to collect images of the plantar surface of the user's feet which, are therefore situated so that when cooperatively affixed a distance from the support of a user's legs from lower extremity support structure 24, will necessarily avoid artifacts or other distortions that would otherwise be present on the image of the plantar surface as a result of such compression. To that end, retention framework 22 is provided for the reception of, and stable (preferably elevated) retention of image acquisition device 20. To this end, retention framework 22 must provide for the accommodation of various types of possible image acquisition device 20, such as cameras, video cameras, webcams, video and/or camera-enabled smart phones, video and/or camera-enabled PDAs, and video and/or camera-enabled tablets and the like. Accordingly, this structure should ideally have a frame or slotted holding structure (not depicted) that can easily accommodate a user sliding or fitting a camera, smart phone, etc. into the frame thereof.

In one embodiment, a directed illumination source (not depicted) and a remote trigger (also not depicted) for triggering the image acquisition device may be provided. Illumination may be provided by ambient light and supplemented by directional LEDs (or other illumination sources). In an alternative embodiment of the present invention, provision may also be made for any images taken by image acquisition device 20 to be transported in either a wired fashion or via a USB port, or wirelessly via Bluetooth® or other wireless protocol, to a monitor interface 28 that is electronically connected to the image acquisition device for real time viewing of images acquired by said image acquisition device by an immediate user. As specifically seen in FIG. 1A and as depicted in use in FIG. 3, monitor interface 28 may be independently situated and may comprise any viewing device, whether a computer, smart television screen, PDA, iPad®, etc. so long as the native software therein would allow the user to see his own feet on an easily visible screen, and which is connected to image acquisition device 20 through either a wired or wireless connection. Alternatively, monitor interface 28 may be optionally affixed to support frame 12 by optional monitor interface support 26, so as to extend therefrom in an outwardly projected fashion (as depicted in FIG. 1B and as depicted in use in FIG. 2), and may comprise any viewing device, whether a computer, smart television screen, PDA, iPad®, etc., so long as the native software therein would allow the user to see his own feet on an easily visible screen. Provision of either variant such ensures that a user can start the self-screening process and can send only quality images given the ability to retake images if needed, and further ensures that the patient or user can always choose which images to send to their health care provider. To this end, either approach to provision of monitor interface 28 ensures that any images acquired by image acquisition device 20 are instantly available for viewing by an immediate user, such as the patient employing the system on his feet. Once chosen, the native software on any of the above mentioned devices will permit the user to send the target images to their doctor via secure methods over the internet or cell phone networks for the doctor's review thereof. When provided as such, should abnormalities become apparent in the images, the users are able to contact their healthcare provider and obtain the appropriate clinical care. Accordingly, as a screening tool, the device is therefore intended to indicate the need for review of the patient's feet by clinicians, thereby prompting patients to physically visit the clinic so that clinicians can address sores before they require extreme treatments.

The device also includes other approaches, such as those outlined in US Pat. Pub. No. 2005/0097762, titled "Device and Method for Examining a Diabetic Foot" and EP Pat. No. 1490651, titled "Compact Optical Contour Digitizer" and related U.S. Pat. No. 7,068,379, titled "Compact Optical Contour Digitizer", each of which are hereby incorporated by reference in their entirety.

The invention being thus described, it will be evident that the same may be varied in many ways. Such variations are not to be regarded as a departure from the spirit and scope of the invention and all such modifications are intended to be included within the scope of the claims.

What is claimed is:

1. A system for screening the skin condition of the plantar surface of the feet comprising:
   a support frame having a front portion, a rear portion, a left portion, a right portion, a top portion, and a bottom portion;
   a lower extremity support structure affixed to said support frame so as to extend upwardly from said top portion of said support frame; and
   an image acquisition device interface affixed to said support frame, proximate to said rear portion of said support frame, said image acquisition device interface comprising retention framework for reception of, and stable retention of, an image acquisition device, said image acquisition device thereby being situated apart from said lower extremity support structure so as to acquire images without artifacts or other distortions.

2. The system for screening the skin condition of the plantar surface of the feet according to claim 1, wherein said support frame further includes an elevation support framework for securely elevating said support frame substantially off a ground surface.

3. The system for screening the skin condition of the plantar surface of the feet according to claim 2, wherein said elevation support framework for securely elevating said support frame substantially off a ground surface is selected from the group comprising either a static elevation stand or a foldable elevation stand.

4. The system for screening the skin condition of the plantar surface of the feet according to claim 3, wherein said elevation support framework for securely elevating said support frame substantially off a ground surface comprises a foldable elevation stand, said foldable elevation stand being hingedly attached to said support frame at said front portion of said support frame.

5. The system for screening the skin condition of the plantar surface of the feet according to claim 4, wherein said lower extremity support structure comprises two substantially parallel stabilizing leg cuffs.

6. The system for screening the skin condition of the plantar surface of the feet according to claim 5, wherein said retention framework provides for reception of, and stable retention of, an image acquisition device and provides for the accommodation of said image acquisition device whereby said image acquisition device can be chosen from the group comprising cameras, video cameras, video/camera-enabled smart phones, video/camera-enabled PDAs, and video/camera enabled tablets.

7. The system fir screening the skin condition of the plantar surface of the feet to claim 6, wherein said support frame is at least partially formed from at least one lightweight material that is chosen from the group comprising aluminum, titanium, fiberglass, or plastic.

8. The system for screening the skin condition of the plantar surface of the feet according to claim 7, further including a source of directed illumination and a remote trigger for triggering said image acquisition device.

9. The system for screening the skin condition of the plantar surface of the feet according to claim 8, further including a monitor interface electronically connected to said image acquisition device for real time viewing by an immediate user of images acquired by said image acquisition device.

10. The system for screening the skin condition of the plantar surface of the feet according to claim 8, wherein said monitor interface is affixed to said support frame and extends therefrom in an outwardly projected fashion, and is electronically connected to said image acquisition device
for real time viewing by an immediate user of images acquired by said image acquisition device.

* * * * *